United States Patent [19]
Akagawa et al.

[11] Patent Number: 5,286,628
[45] Date of Patent: Feb. 15, 1994

[54] MONOCLONAL ANTIBODIES TO MITE ALLERGEN AND THE USE THEREOF

[75] Inventors: Midori Akagawa; Yachiko Hayashi; Toshio Mori, all of Tokyo; Satoshi Sugiyama, Chiba; Tohru Andoh, Funabashi, all of Japan

[73] Assignees: Asahi Breweries, Ltd.; Torii & Co., Ltd., both of Tokyo, Japan

[21] Appl. No.: 798,483

[22] Filed: Nov. 26, 1991

[30] Foreign Application Priority Data

Feb. 6, 1991 [JP] Japan ..................................... 3-35018

[51] Int. Cl.$^5$ ..................... G01N 33/53; C07K 15/14; C12N 5/12
[52] U.S. Cl. ..................................... 435/7.21; 435/7.9; 435/7.92; 435/240.27; 435/810; 435/975; 530/388.1; 530/388.2; 530/391.1; 530/391.3
[58] Field of Search ....................... 435/7.21, 7.9, 7.92, 435/7.93, 7.94, 7.95, 8, 810, 975, 240.27; 436/531, 518, 548, 824, 86, 800, 815, 543; 530/388.1, 388.2, 391.1, 391.3

[56] References Cited

U.S. PATENT DOCUMENTS 4,281,061  7/1981  Zuk et al. ................................ 435/7

OTHER PUBLICATIONS

Platts–Mills, et. al., "Dust mite allergens and asthma–A worldwide problem", *J. Allergy Clin. Immunol.*, 83 (2/1): 416–427 (1989).
Chapman, "Mite allergens and asthma", *Current Opinion in Immunology*, 2:525–530 (1990).
Platts–Mills, et al., "Dust mites: Immunology allergic disease, and environmental control", *The Journal of Allergy and Clinical Immunology*, 80(6): 755–775 (1987).
Heymann, et al., "Antigenic and Structural Analysis of Group II Allergens (Derf II and Derp II)", *The Journal of Allergy and Clinical Immunology*, 83(6): 1055–1067 (1989).
Stewart, et al., "The Molecular Characterization of Mite Allergens", *International Symposium on Mite and Midge Allergy*, Tokyo, 146–169 (1988).
Lind, "Enzyme–Linked Immunosorbent Assay for Determination of Major Excrement Allergens of House Dust Mite Species D. pteronyssinus, D. farinae and D. microceras", *Allergy*, 41:442–451 (1986).
Kimura, "ELISA inhibition method in detection of mite and chironomid antigens in environmental samples of dust, soil and air", *Allergy*, 45:167–173 (1990).
Chapman, "Allergen specific monoclonal antibodies: new tools for management of allergic disease", *Allergy*, 43: (supp. 5) 7–14 (1988).
Yasueda, et al., "Measurement of Allergens Associated with Dust Mite Allergy", *Int. Arch. Allergy Appl. Immunol.*, 90: 182–189 (1989).
Sakaguchi, et al., "Measurement of Allergens Associated with Dust Mite Allergy", *Int. Arch. Allergy Appl. Immunol.*, 90: 190–193 (1989).
Konishi, et al., "ELISA for Quantifying Antigens of Dermatophagoides farinae and D. pteronyssinus in House Dust Samples", *Journal of Medical Entomology*, 27(6): 993–998 (1990).
Luczynska, et al., "A two–site monoclonal antibody ELISA for the quantitation of the major Dermatophagoides spp. allergens", *Journal of Immunological Methods*, 118: 227–235 (1989).
Yasueda, et al., "Isolation and characterization of two allergens from Dermatophagoides farinae", *Int. Arch. Allergy Appl. Immunol.*, 81: 214–223 (1986).
Harlow and Lane, *Antibodies, A Laboratory Manual.* Cold Spring Harbor Laboratory, New York. (1988) See chapters 6 and 14, especially.
Hemmila, I., *Clin. Chem.* vol. 31 (3) pp. 359–370 (1985).

*Primary Examiner*—Toni R. Scheiner
*Attorney, Agent, or Firm*—Browdy and Neimark

[57] ABSTRACT

The invention provides an anti Derf II monoclonal antibody selectively recognizing Derf II and belonging to an IgG or IgM class, the antibody being obtained by immunizing a mammal with Derf II antigen, which is derived from *Dermatophagoides farinae*.

4 Claims, 8 Drawing Sheets

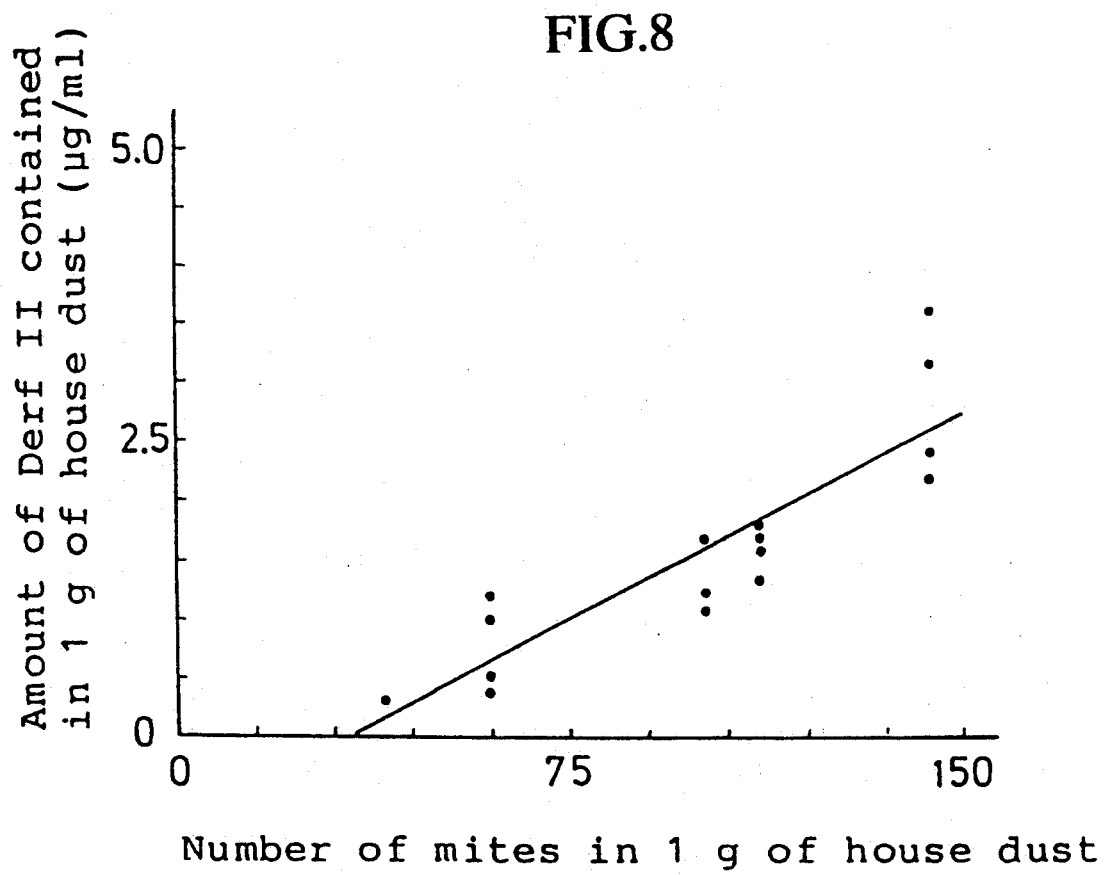

MONOCLONAL ANTIBODIES TO MITE ALLERGEN AND THE USE THEREOF

BACKGROUND OF THE INVENTION

The present invention relates to monoclonal antibodies specific for Derf II which is a major allergen of house dust mite *Dermatophagoides farinae*, cell lines for producing the antibodies, immunoassays in which the monoclonal antibodies are used, and purification of Derf II.

House dust is a major allergen of bronchial asthma, allergic rhinitis and the like. It is said that the allergen is caused by mites (Sakamoto, Kagaku to Seibutsu, Vol. 26, No. 2 (1988), Voorhoost, R. et al, J. Allergy, 39, 325 (1967)) and at least 90% of people who are positive in a patch test of house dust are also positive to mites (Hayakawa and Shida, Nippon Rinsho, Vol. 45, No. 8 (1987)). The mites, which are important as a cause of allergens, are *Dermatophagoides farinae* and *Dermatophagoides pteronyssinus* (T. Miyamoto et al., J. Allergy, 42, 14 (1968)). In *Dermatophagoides farinae*, there are two major allergens named Derf I (molecular weight 24,000) and Derf II (molecular weight 15,000–16,000). Derf I is contained in mite feces and Derf II is contained in mite bodies (and the dead bodies and their body pieces).

It is generally important to identify the original allergen in medical treatment of allergic disease. It is effective to clinically guide a patient so as to avoid the original allergen (Sakamoto, Kagaku to Seibutsu, Vol. 26, No. 2 (1988), Platts-Mills, T. A. E., J. Allergy, 83, 416–427 (1989)). Then, quantification and determination of the mite allergen in surroundings of the patient are required. Therefore, methods for detecting mite allergens in house dust have been proposed.

In these methods, a color reaction of a protein, which is derived from feces of house dust mites and extracted with alcohol, and an aromatic diazo compound (Japanese Patent Laid-open Publication Nos. 60-135844, 60-171459 and 61-59261) is not conducted by a simple process. Though the presence of a mite allergen is recognizable by the reaction, it is impossible to identify and determine the allergen. In a color reaction of body fluid of a small animal and chemicals (Japanese Patent Laid-open Publication Nos. 62-296828 and 62-296829), though the operation is simple, it is impossible to identify and determine a mite allergen because small animal allergens other than the mite allergen are detected. Further in a detection method wherein anti-serum obtained by immunizing an extract of mite bodies to an animal is used (Japanese Patent Laid-open Publication No. 63-191961), though it is possible to detect and determine living bodies of dust mites, detection and determination of the dead bodies, pieces and feces remain unexplained, and it is impossible to identify and determine the allergen.

In treatment of mite allergy, desensitization therapy is generally conducted by using a mite allergen extract. The therapy needs to determine and purify the allergen to be given (Eda, Nippon Rinsho, Vol. 44, a special number, 1986). In this regard, specificity of monoclonal antibodies which have been prepared from mammals immunized by mite bodies or feces is unknown.

SUMMARY OF THE INVENTION

Objects of the present invention are to solve the above problems in the identification and determination of allergens, to provide a simple and highly sensitive method for immunologically identifying and determining Derf II in dust, to suggest the possibility of counting of dust mites, and to provide a simple method for purifying Derf II in samples in high purities.

Inventors of the present invention have prepared monoclonal antibodies which are specific for Derf II and investigated an immunoassay by using the antibodies. As a result, they found that the monoclonal antibodies were useful as a reagent for determining Derf II and attained to the present invention. Namely, the present invention provides a method for identification, determination and qualification of Derf II in samples, characterized in that a monolonal antibody which can be specifically bound to Derf II is used.

The monoclonal antibody of the present invention can be prepared by a well-known cell fusion method. In detail, the monoclonal antibody of the present invention is obtained by the following steps (1) to (4):

(1) a step for preparing antibody-producing cells,
(2) a fusion, screening and cloning steps,
(3) a hybridoma-culturing step, and
(4) if necessary, a purification step.

The following description illustrates the steps in detail.

(1) Step for preparing antibody-forming cells

Anti Derf II antibody-producing cells can be prepared from the spleen of a Balb/c mouse or an A/J mouse to which an antigen of Derf II is adequately immunized. A mixture of 10–30 µg/mouse of Derf II and the same amount of complete Freund's adjuvant or incomplete Freund's adjuvant are intraperitoneally administered, and it is repeated at intervals of two to four weeks. After confirming that the antibody titer in blood is sufficiently elevated, the same amount of Derf II without the above adjuvant is intraperitoneally administered or intravenously injected in the mouse tail and the mouse is finally immunized. Two to five days from the final immunization, the antibody-producing cells are prepared from the spleen of the mouse.

(2) Fusion, screening and cloning steps

In the fusion step, the above mouse antibody-producing cells and well-known mouse myeloma cells are fused by a conventional method in the presence of a fusion-enhancing agent.

The myeloma cells which can not develop in a hybridoma selective medium and do not produce antibodies are generally preferred. Such mouse myeloma cells are, for example, mouse myeloma cell P3-NS1-1-Ag4-1 (abbreviated as NS-1 hereinafter), Sp-2/0-Ag14 (abbreviated as SP-2) and similar cells.

The ratio of the myeloma cells to the antibody-producing cells is usually 1 to 1–20. As the cell fusion-enhancing agent, for example, polyethylene glycol having a molecular weight of 1000–7500 are preferably used. The culture of the hybridomas is conducted as follows: for example, after the hybridoma is washed to remove the cell fusion-enhancing agent, each 100–200 µl of the hybridoma suspension in the hybridoma selective medium is seeded into 96 wells of a plate in an atmosphere of 5% $CO_2$ gas-air at a temperature of about 37° C.

The screening of the desired hybridomas is conducted by determining the antibody titer in the culture solution. Namely, after Derf II is bound to each well of the assay plate and the wells are blocked with bovine serum albumin, the supernatant of the culture in which the hybridomas are sufficiently grown is added to each well of the assay plate. After adequate incubation and antigen-antibody reaction in the wells, the supernatant is removed and the plate is washed. Then, an avidin-labeled anti-mouse IgG antibody is added to the wells, the plate is washed, biotin-labeled alkaline phosphatase is added to the wells, the plate is washed and each well is colored by adding p-nitrophenylphosphate of a substrate.

Hybridomas whose antibody production is positive are cloned by a limiting dilution and the desired hybridoma clone can be prepared.

(3) Hybridoma-culturing step

The cloned hybridoma obtained in the above steps is cultured in vitro or in vivo and the desired monoclonal antibody can be prepared. The culture in vitro begins with a 96 well plate to obtain some hybridomas and the scale-up is gradually conducted. The culture in vivo is conducted by intraperitoneally inoculating the hybridoma to a mouse treated with pristane (2, 6, 10, 14-tetramethylpentadecane: manufactured by Aldrich Company) which is used to easily propagate the fused cells. After 7-15 days, ascites containing the monoclonal antibody are accumulated in vivo.

(4) Purification step

The purification step is conducted when necessary. In the step, the monoclonal antibody obtained in the purification above steps may be purified by a combination of conventional physico-chemical techniques, for example, salting-out, centrifugation, dialysis, ion-exchange chromatography and the like. When the antibody subclass of the monoclonal antibody is IgG1, it is insufficiently recovered by absorption and elution with a protein A column which is used in the other subclasses, and it is conveniently well-recovered by absorption and elution with a protein G column.

In the present invention, several kinds of monoclonal antibodies which recognize Derf II can be obtained by the above steps.

It becomes possible to conduct well-known immunoassays such as a competition method, a sandwich method and the like by using the monoclonal antibodies which are able to specifically combined to Derf II obtained by the above steps.

As an example, in the immunoassay of the sandwich method, the antibodies may be immobilized on a solid phase by a conventional method. As the solid phase, for example, a microtiter plate and particles prepared with polystyrene, polyethylene, polyvinyl chloride, latex, agarose, cellulose, methacrylate, glass and the like are preferably used.

Moreover, conventional methods are used as a method for labeling the antibody without any restriction. For example, any one of enzymes, fluorescent dyes, chemical luminous materials and radioisotopes or a combination of these compounds is employed.

As a labeling agent, peroxidase, $\beta$-D-galactosidase and alkaline phosphatase and the like are usable in a process using the enzyme, $^{125}I$, $^3H$ and the like are usable in a process using the radioisotope, and fluorescamine, fluorescein isothiocyanate and the like are usable in a process using the fluorescent dye. However, the other compounds may be used in the above processes.

When the labeling agent is the enzyme, a substrate is used for determining an activity of the enzyme. As an example, 2, 2-azinodi-(3-ethylbenzthiazolin sulfonic acid)-2 ammonium salt-$H_2O_2$, 5-aminosalicylic acid-$H_2O_2$, o-phenylenediamine-$H_2O_2$ or the like is usable as a substrate of peroxidase, o-nitrophenyl $\beta$-D-galactopyranocide is usable as a substrate of $\beta$-D-galactosidase and p-nitrophenylsulfonyl phosphate is usable as a substrate of the alkaline phosphatase. To determine the activity, a well-known reagent such as a solvent, a washing agent, a reaction terminator and the like may be used. An immunoassay kit using the reagents is included in the present invention.

Immunoassay using a sandwich method is characterized in that the first monoclonal antibody recognizing a material (antigen) to be determined and the second monoclonal antibody recognizing an antigen determinative site which is different from the first monoclonal antibody are used, the first monoclonal antibody is immobilized on a solid phase and the second monoclonal antibody is labeled.

According to the present invention, a monoclonal antibody which can be specifically bound to Derf II is obtained. It also provides highly sensitive determination of Derf II having a low concentration of 10-300 ng/ml. The immunoassay of the present invention is a method for specifically determining Derf II. The method is very simple in comparison with conventional methods using chemical reaction. It provides a much more sensitive and specific method for detecting Derf II than a conventional method using a monoclonal antibody obtained by immunizing dust mites. Moreover, it becomes possible to highly and simply purify Derf II in samples by using monoclonal antibodies obtained by the present invention.

Figure 1:
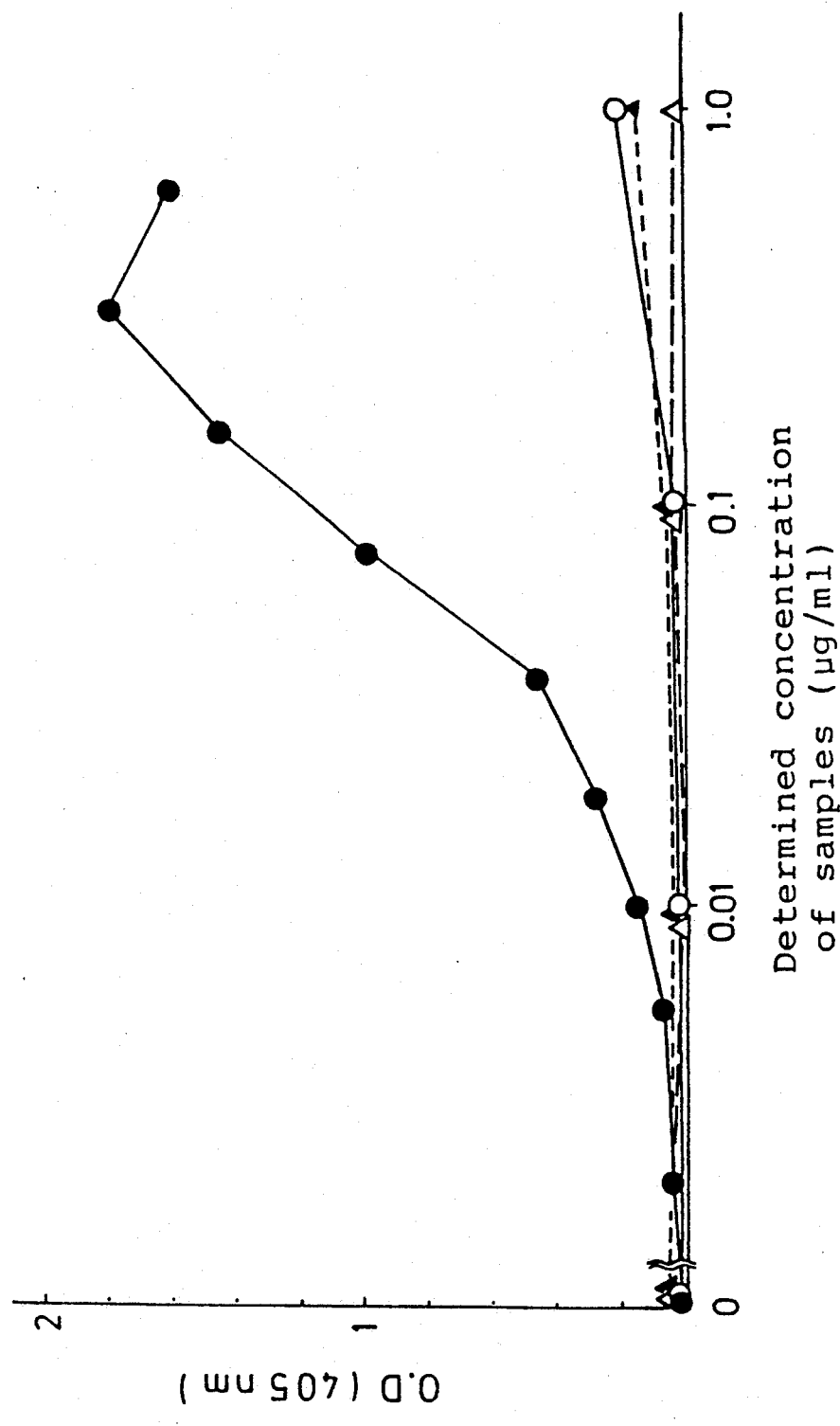
FIG. 1 shows a graph of calibrations of purified Derf I, Derf II, Derp I, Derp II obtained in (4) of Example 1, the axis of ordinate shows O.D. values at a wave length of 405nm and the axis of abscissa shows determined concentrations of samples ($\mu$g/ml). Closed circle: Derf II, open circle: Derf I, open triangle: Derp I and closed triangle: Derp II.

Lane 1 : marker, Coomassie Brilliant Blue (C.B.B.) dyeing, lane 2 : Derf II, C.B.B. dyeing, lane 3 : freeze-dried powder of mite bodies, C.B.B. dyeing, lane 4 : Derf II 13A4, lane 5 : Derf II 15E11, lane 6 : Derf II 18G8, lane 7 : mite freeze-dried powder 13A4, lane 8 : mite freeze-dried powder 15E11, and lane 9 : mite freeze-dried powder 18G8.

Figure 3A:
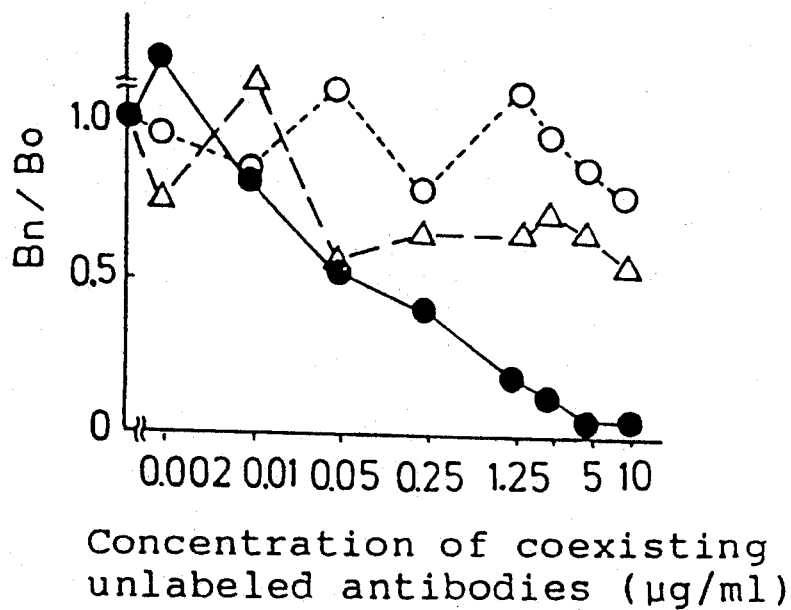
Figure 3B:
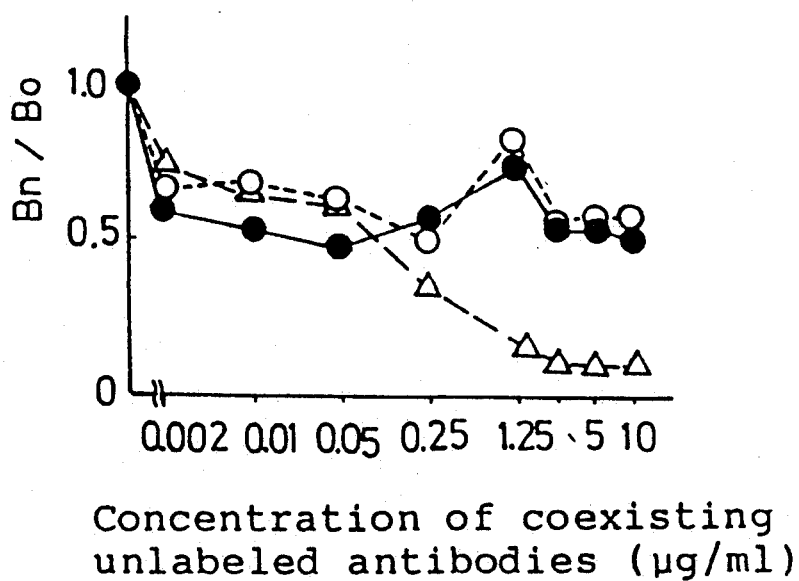

FIGS. 3A and 3B show a graph of O.D. values obtained in Example 4 by reacting labeled antibodies, the axis of ordinate shows Bn/Bo values in which Bo is an O.D. value obtained by reaction of the labeled antibody alone and Bn is an O.D. value obtained from each concentration of coexisting unlabeled antibodies. The axis of abscissa shows concentrations of the coexisting unlabeled antibodies ($\mu$g/ml).

FIG. 3A is in the case of a competition of 13A4* vs. the unlabeled antibodies and FIG. 3B is in the case of a competition of 18G8* vs. the unlabeled antibodies. Open circle is 15E11, closed circle is 13A4 and open triangle is 18G8.

Figure 4:
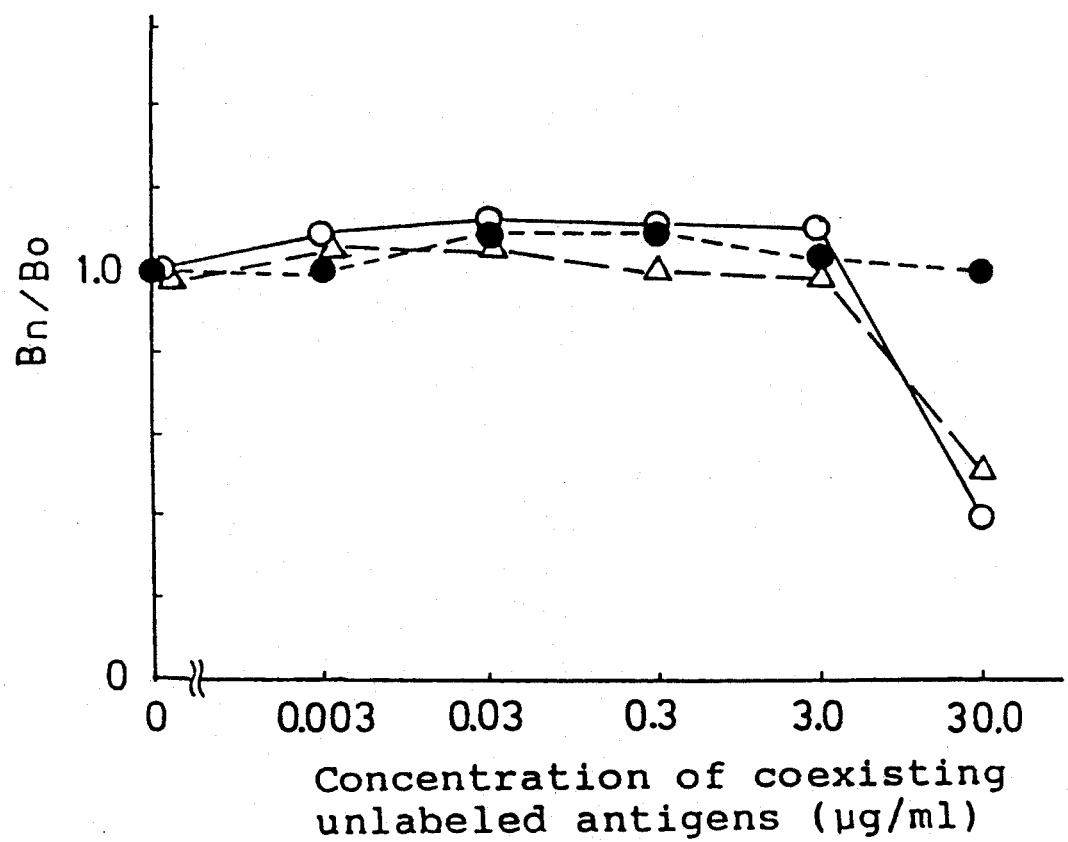

FIG. 4 shows a graph of the results obtained by determination of ranges in which Derf II alone was detected in the presence of Derf I (open circle), Derp I (closed circle) and Derp II (open triangle) obtained in Example 5. The axis of ordinate shows Bn/Bo values in which Bo is an O.D. value of Derf II alone and Bn is an O.D. value obtained from each concentration of coexisting other antigens. The axis of abscissa shows concentrations of the coexisting antigens (μg/ml).

Figure 5:
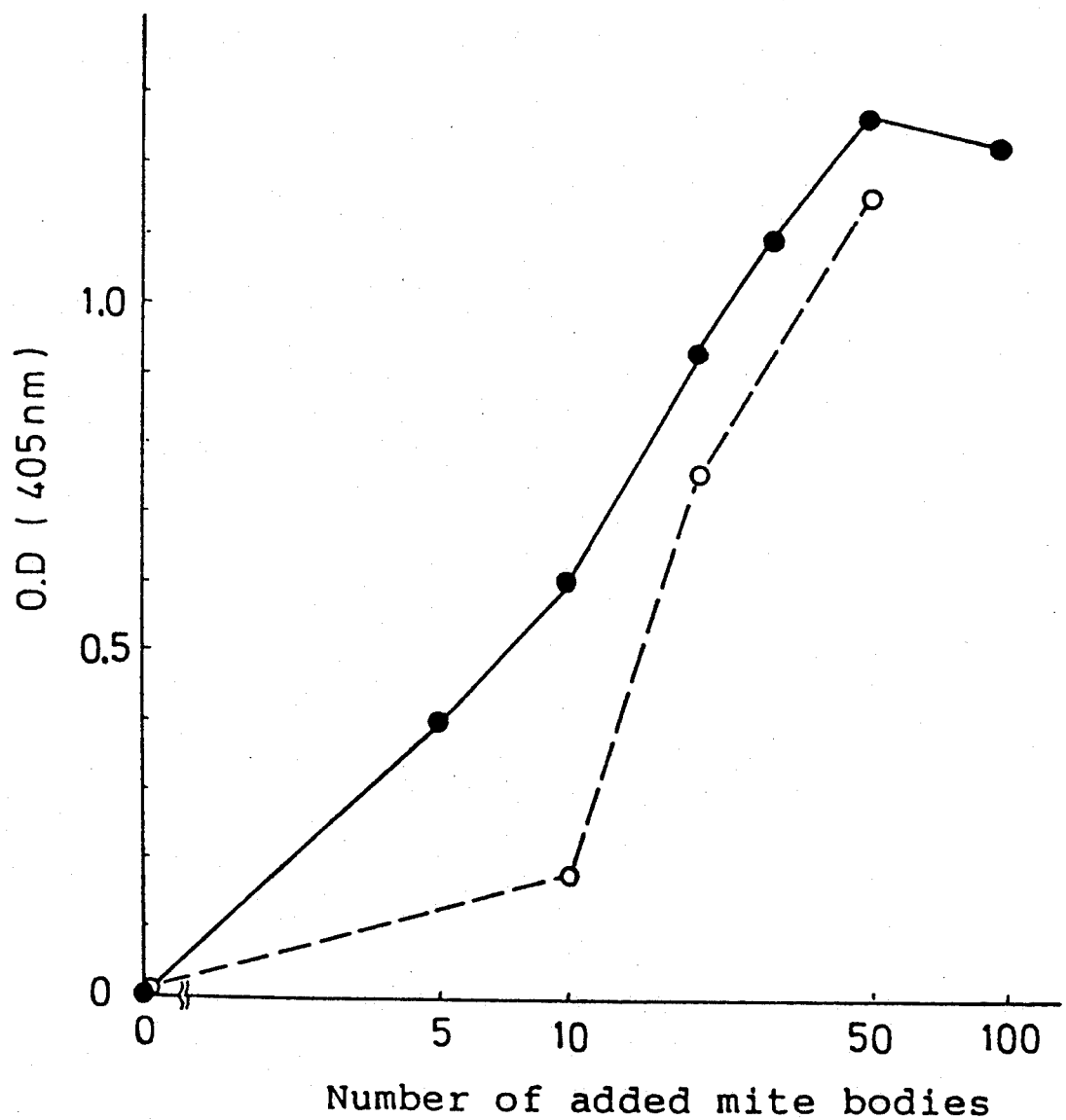

FIG. 5 shows a graph showing the relation of the numbers of house dust mites and the absorbance obtained in Example 6. The axis of ordinate shows the O.D. value in a wavelength of 405 nm. The axis of abscissa shows the numbers of the added mite bodies. Closed circle is in the case of PBS-Tween extraction, and open circle is in the case of PBS extraction.

Figure 6:
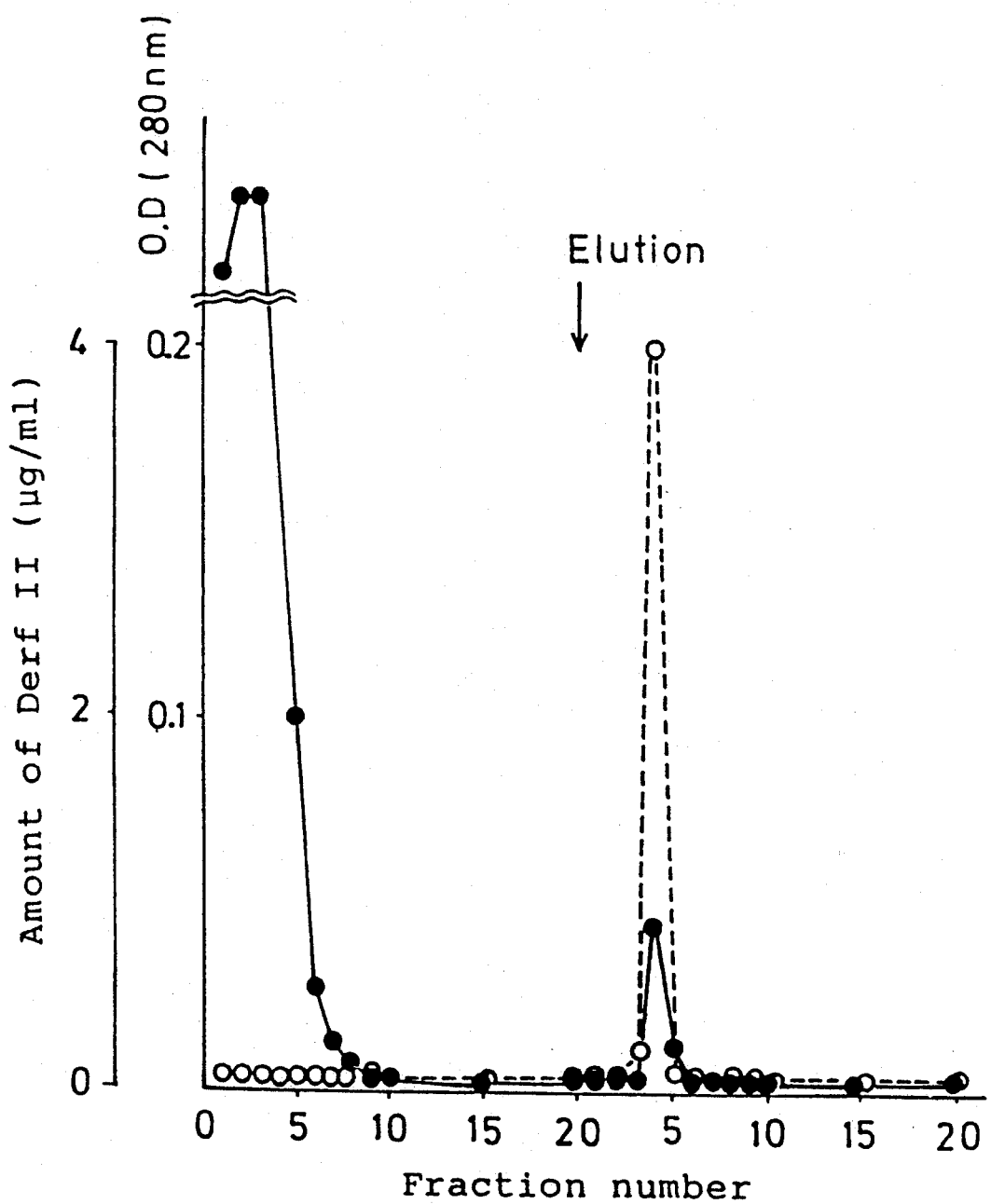

FIG. 6 shows a graph showing purification of Derf II in the fractions obtained in Example 7, the axis of ordinate shows O.D. values (closed circle) in a wavelength of 280 nm, or amounts of Derf II (μg/ml) (open circle) contained in the fraction which is determined from an ELISA system. The axis of abscissa shows fraction numbers.

Figure 7:
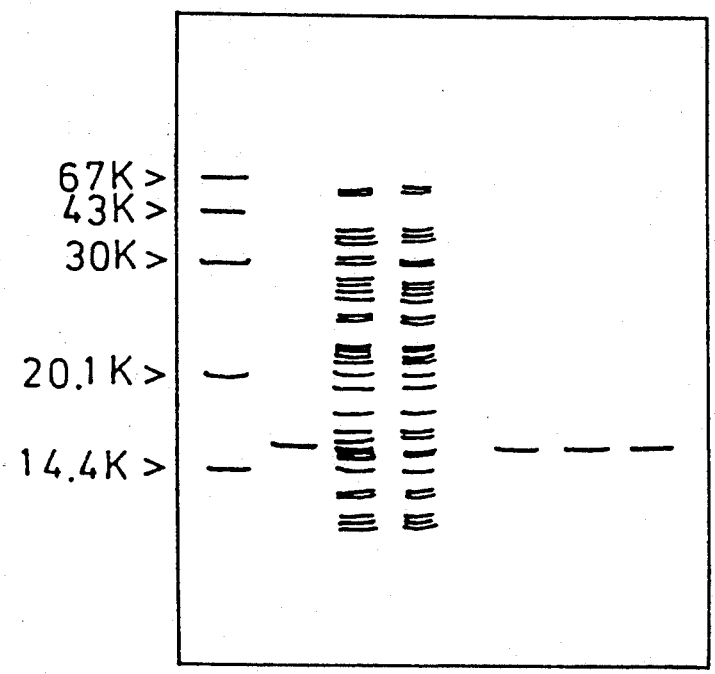

FIG. 7 shows SDS-PAGE silver staining of the fraction obtained in Example 7, lane 1 shows a standard marker, lane 2 shows standard Derf II, lane 3 shows a solution of freeze-dried powder of mite bodies, lanes 4 and 5 show column unadsorbed fractions (the fraction numbers are referred to FIG. 6), lanes 6,7 and 8 show purified fractions obtained by eluting adsorbed fractions from a column (the fractions are referred to FIG. 6).

FIG. 8 shows a graph of correlation between amounts of Derf II and numbers of mites in house dust samples. The axis of ordinate shows amounts of Derf II (μg/ml) contained in 1 g of house dust determined by ELISA, the axis of abscissa shows numbers of mites in 1 g of the house dust. n=16, and coefficient of correlation r=0.884.

DESCRIPTION OF PREFERRED EMBODIMENTS

The following examples illustrate the present invention in detail. However, these examples are not to be construed to limit the scope of the invention.

EXAMPLE 1

(1) Preparation of anti Derf II monoclonal antibodies

Anti Derf II monoclonal antibodies were prepared by the following method.

a) Immunization

House dust mites were collected by a floatation of them in a saturated saline solution, and the mites were extracted with phosphate-buffered saline (abbreviated as PBS hereinafter). The extract was separated with a 60% saturated ammonium sulfate solution. After removing a precipitate, the supernatant solution was applied on a DEAE-Sephacell (0.05M Tris Cl, pH8.0) and the nonadsorbed fraction was applied on a S-Sepharose (0.02M acetate buffer, pH5.5 ~ 0.2M NaCl (linear gradient)). The 80 mM NaCl elution fraction was applied on a Sephadex G-75 and the peak fraction was recovered as crude purified Derf II antigen for immunization.

The same amounts of the crude and complete Freund's adjuvant (FCA, manufactured by Difco) were mixed and emulsified to obtain 30 μg/100 μl (10 μg/100 μl for A/J mouse) of Derf II. The mixed emulsion was administered intraperitoneally 30 μg to Balb/c mice (males) and 10 μg/mouse to A/J mice (males). At intervals of about 2 to 4 weeks, the same amount of the emulsified Derf II in incomplete Freund's adjuvant (FIA, manufactured by Difco) was intraperitoneally administered five times to immunize the mice. In the last immunization, PBS containing 30 μg of Derf II was administered in the mouse tails of Balb/c mice (PBS containing 5 μg of Derf II was intraperitoneally administered to the A/J mice) of which the antibody titer in blood becomes positive three days before the cell fusion (when the concentration of the serum was diluted to 1/1000 times or less, immunoassay of the Derf II solid phase was positive).

b) Preparation of cells

Three days from the final immunization, the spleen of the mouse was picked up, the spleen cells were dispersed in RPMI medium containing 10% fetal bovine serum (FLOW Lab. Co., LTD, abbreviated as RPMI hereinafter), the mixture was filtered with 200 m/s stainless mesh and the cells were washed three times with RPMI medium which was free from fetal bovine serum (abbreviated as −RPMI hereinafter). NS-1 for the Balb/c mice and SP-2 for the A/J . mice were used as mouse myeloma cells of fusion partners.

The cells were cultured until one week before the cell fusion with RPMI to which 30 μg/ml of 8-azaguanine was previously added. Then, logarithmic growth cells cultured with RPMI were washed three times with −RPMI.

c) Cell fusion and selection of antibody-producing hybridomas $1-2 \times 10^8$ cells of spleen cells and myeloma cells were mixed in the ratio of about 5:1 and centrifuged to obtain pellets. One ml of -RPMI containing 50% of polyethyleneglycol (PEG 4000, Kanto Kagaku) was added dropwise for one minute and stirred for another one minute. Eight ml of RPMI was added to the mixture with stirring for eight minutes. After adding 10 ml of RPMI, the mixture was centrifuged and the pellets obtained were suspended to obtain a concentration of $5 \times 10^6$/ml of spleen cells and the suspension was seeded on a 96 well plate (manufactured by Sumitomo Bakelite Company) in the ratio of 100 μl/well. From the next day, RPMI containing 0.1 mM of hypoxanthine, 0.4 μM of aminopterin and 16 μm of thymidine (abbreviated as HAT medium hereinafter) was added in the ratio of 100 μl/well. Then, about one to two weeks after each 100 μl of the HAT medium was changed for 100 μl of fresh HAT medium before colony of hybridomas was appeared, anti Derf II antibodies were detected and cells of positive wells were cloned by limiting dilution. After the cells were cultured with RPMI containing 0.1 mM of hypoxanthine and 16 μM of thymidine, the second limiting dilution were conducted and cloning was conducted. Then, hybridomas producing anti Derf II monoclonal antibodies were obtained.

d) Production of monoclonal antibodies

After the cloned hybridomas producing monoclonal antibodies were propagated with RPMI, the hybridomas were transplanted intraperitoneally Balb/c mice in which 0.5 ml of pristan was injected two weeks ago (in the case of hybridomas derived from A/J mice, the hybridomas were transplanted intraperitoneally CAF-1 mice) in the ratio of $10^6$–$10^7$ cells/mouse. After two weeks, ascites which were accumulated in the abdomen were collected and monoclonal antibodies from the ascites were purified.

e) Purification of monoclonal antibodies

The ascites were centrifuged at 10,000 rpm for 20 minutes to remove precipitates and filtered with a sterilized filter (MILLEX (trade mark) 0.3 μm, Milipore Ltd.). The protein concentration of the filtrate was determined by a Lowry method.

The filtrate containing 100 to 150 mg of protein was applied on a Protein G column kit (Mab Trap G, manufactured by Pharmacia Company), the purified fraction was dialyzed against PBS. The purity of dialyzed solution was examined by sodium dodecyl sulfate-polyacrylamide gel electrophoresis (abbreviated as SDS-PAGE hereinafter). After confirming a single band by Westernblot, purified monoclonal antibodies were obtained.

In the monoclonal antibodies obtained, six types were deposited to Fermentation Research Institute (FRI), Agency of Industrial Science and Technology, Ministry of International Trade and Industry in Japan based on Budapest Treaty. The deposit numbers are as follows.

| Identification symbols named by the depositor | Deposit numbers |
|---|---|
| 1B2 | FERM 3247 (BP-3247) |
| 7C10 | FERM 3248 (BP-3248) |
| 15E11 | FERM 3249 (BP-3249) |
| 18G8 | FERM 3250 (BP-3250) |
| 13A4 | FERM 3251 (BP-3251) |
| 24B7 | FERM 3252 (BP-3252) |

(2) Preparation of antibody-coated plates

To each well of an untreated 96 well micro titer plate (Immulon 1, manufactured by Dynatech Laboratories Inc., abbreviated as a micro titer plate), 50 µl of a PBS solution dissolving 5 µg/ml of 15E11 which is a mouse anti Derf II monoclonal antibody was added and the plate was incubated for two hours at room temperature. Then, the solution was removed from each well, the plate was washed with PBS containing 0.05% Tween 20 (abbreviated as PBS-Tween hereinafter) three times and it was blocked with PBS containing 1% BSA or 1% Tween 20 at room temperature for one hour (or at 4° C. overnight). The plate washed with PBS-Tween three times was used. It was possible to store the plate at a low temperature of −30° C.

(3) Preparation of bovine pancreatic alkaline phosphatase labeled antibodies 5 mg of bovine pancreatic alkaline phosphatase (EIA grade: manufactured by Boehringer Mannheim Company) was added to 1.7 mg of purified monoclonal antibodies, and the mixture was dialyzed against PBS overnight. The volume of the dialysate was determined and 1/10 volumes of 20% glutaraldehyde (Wako Pure Chemical Industries, Ltd.) was added to the dialysate and the mixture was stirred for two hours at room temperature. After the solution was collected and dialyzed against PBS overnight, it was dialyzed against 0.25M Tris-HCl at pH 8.0 overnight to obtain a labeled antibody solution. Sodium azide was added to the solution at a final concentration of 0.02% and the solution was stored at 4° C.

(4) Calibration with purified Derf I and purified Derf II

To a microtiter plate coated with 15E11 which is a monoclonal antibody prepared by the method described in (2), 50 µl of PBS (or PBS-Tween) containing 0-0.3 µg/ml or purified Derf II was added. 50 µl of PBS (or PBS-Tween) containing 0-0.3 µg/ml of another allergen Derf I (molecular weight: 24K) derived from *D. farinae* and allergen Derp I (molecular weight: 24K) or Derp II (molecular weight: 15K) derived from *D. pteronyssinus* was added to each well as a specific binding control. After incubating for two hours, the wells were washed three times with PBS-Tween and 50 µl of a solution of alkaline phosphatase-labeled anti Derf II prepared in (3) (abbreviated as 13A4*) with PBS (or PBS-Tween) in the ratio of 9 µg/ml was added to the wells. After incubating for two hours, the wells were washed with PBS-Tween and 100 µl of a substrate solution containing in the ratio of 5 ml of diethanolamine buffer pH 9.8 and a substrate tablet (1 mg, manufactured by Sigma Chemicals, Co.) (the solution is abbreviated as a substrate solution, hereinafter) was added to each well. The colored wells were allowed to react at room temperature for ten minutes and 50 µl of 5N NaOH was added to stop the reaction. The absorbance of each well was determined at a wavelength of 405 nm with a micro auto reader (manufactured by Corona Company, abbreviated as an autoreader, hereinafter) and the results are shown in FIG. 1.

EXAMPLE 2

Relation of determination of Derf II in a sample and numbers of mite bodies was examined with the anti Derf II monoclonal antibodies obtained in (1) of Example 1.

The monoclonal antibody 15E11 prepared by the method described in (1) and (2) of Example 1 was coated on a microtiter plate. 50 µl of the purified Derf II (0-300 ng/ml) or supernatants of samples were added to each well of the plate. The samples contained human hairs (5 mg), hairs of a dog for breeding outdoors (5 mg), hairs of a dog for breeding indoors (4 mg), hairs of a pet cat (1 mg) and cotton (5 mg) to which 50 mites (*D. farinae*) were added or mites were not added, respectively. The supernatants of samples were obtained by adding 500 µl of PBS-Tween to a detecting sample, stirring for 10 seconds, allowing the mixture to stand for 10 minutes and centrifuging the mixture for two minutes at 10,000 rpm. The wells were incubated for two hours at room temperature and washed with PBS-Tween three times. 13A4* prepared in (3) was diluted with PBS-Tween to obtain a concentration of 9 µg/ml. The diluted solution were added in the ratio of 50 µl per well. the wells were washed with PBS-Tween three times and colored by adding 100 µl of the substrate solution. After the wells were reacted at room temperature for ten minutes, 50 µl of 5N NaOH was added to each well and the reaction was stopped. The absorbance of each well was determined at a wavelength of 405 nm with an autoreader and the results are shown in Table 1.

TABLE 1

| Sample | free from mites | 50 mites added |
|---|---|---|
| rat hair | 0 | 1.12 |
| sanitary cotton | 0 | 1.39 |
| cotton | 0 | 1.18 |
| human hair | 0 | 1.36 |
| dog hair | 0 | 1.17 |
| cat hair | 0 | 1.29 |
| PBS | 0 | 1.17 |

Table 1 shows the relation of determination of Derf II and numbers of mite bodies in the presence of the other materials obtained in Example 2. When mites are not added, O.D. values of each sample is 0 at a wavelength of 405 nm. On the other hand, when 50 mites are added, O.D. value of each sample is almost the same value as that of the control obtained by adding mites to PBS.

EXAMPLE 3

Three kinds of anti Derf II monoclonal antibodies obtained in (1) of Example 1, 18G8, 13A4 and 15E11, were employed to conduct western blot technique for the freeze-dried mite bodies (*D. farinae*) and the purified Derf II.

Figure 2:
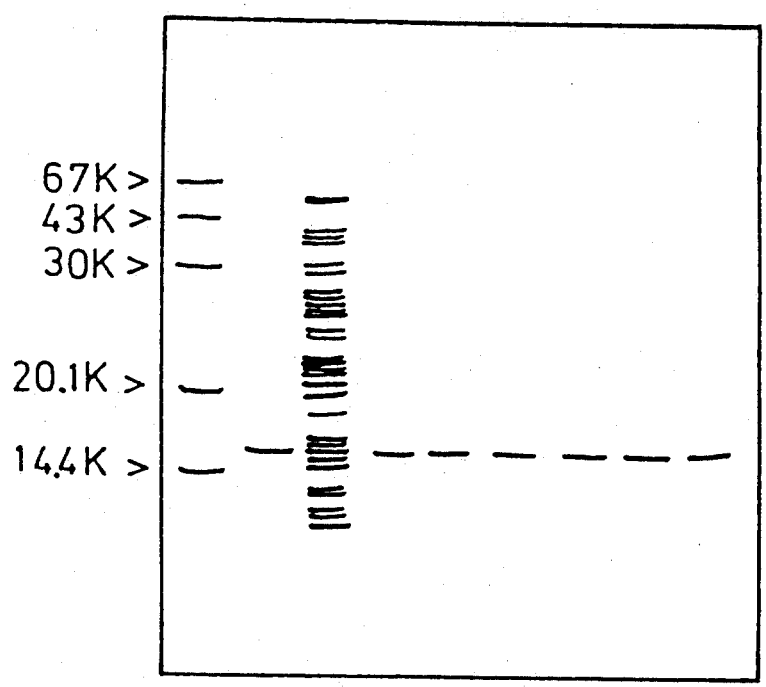
FIG. 2 shows a result of western blot technique of purified Derf II and freeze-dried powder of mite bodies which were obtained in Example 3.

10 mg of the freeze-dried mite bodies (*D. farinae*) was dissolved in one ml of PBS. Six µg/ml of the purified Derf II in PBS was prepared. Each sample was treated with SDS in the presence of β-mercaptoethanol by a well-known method. Twenty µl of the former sample and 10 µl of the latter sample were electrophoresed with 20% poly-acrylamide gel (SDS-PAGE minigel, manufactured by TEFCO Company) at 20 mA for 1.5 hours. After the electrophoresis, each sample was transferred to a blotting paper (PVDF: manufactured by Milipore Ltd.) at 160 mA for one hour. Then, the blotting paper was blocked with PBS containing 3% BSA at room temperature for one hour and washed with PBS-Tween. Monoclonal antibodies 18G8, 13A4 and 15E11 were diluted with PBS containing 2 mg/ml of BSA to obtain a concentration of 50 µg/ml, respectively. The blotting paper was cut and each piece was immersed in each antibody solution and allowed to react at 4° C. overnight. The pieces of the blotting paper were washed with PBS-Tween, the pieces were immersed in a peroxidase-labeled anti-mouse IgG (anti-mouse IgG-HRP, manufactured by Bio-Rad Laboratories) diluted with PBS containing 2 mg/ml of BSA for 2 hours. After washing with PBS-Tween, the pieces were immersed and colored in a solution of 4-chloro-2-naphthol as a substrate. The results are shown in FIG. 2.

EXAMPLE 4

To estimate the distinction of antigen recognition sites among antibodies, three kinds of anti Derf II monoclonal antibodies obtained in (1) of Example 1, 18G8, 13A4 and 15E11, and 18G8* and 13A4* which were labeled with alkaline phosphatase were prepared, and then a competitive examination was conducted.

To each well of micro titer plate, 50 µl of a solution in which the purified Derf II was diluted with PBS in a concentration of 30 µg/ml was added. Each well was incubated at room temperature for two hours and washed with PBS-Tween three times. A solution having a certain concentration of 18G8* (9 µg/ml) and a solution which was prepared with PBS in the presence of unlabeled 18G8, 13A4 or 15E11 in a concentration of 0–10 µg/ml were added to other wells in an amount of 50 µl, respectively. In the same manner, a solution having a certain concentration of 13A4* (9 µg/ml) and a solution which was prepared with PBS in the presence of unlabeled 18G8, 13A4 or 15E11 in a concentration of 0–10 µg/ml were added to other wells in an amount of 50 µl, respectively. The wells were incubated at room temperature for two hours and washed with PBS-Tween. 100 µl of a substrate solution was added to each well to react at room temperature for two hours. 50 µl of 5N NaOH was added to each well to stop the reaction. The absorbance was determined at a wavelength of 405 nm with an autoreader. The results show that a competitive reaction is not observed 13A4 vs. 15E11, but is observed 18G8 vs. 13A4, and 18G8 vs. 15E11. Accordingly, 13A4 and 15E11 apparently recognize different epitope each other (referred FIG. 3).

EXAMPLE 5

By the immunoassay using monoclonal antibodies 15E11 and 13A4* which were employed in Example 2, concentration wherein only Derf II was detected in the presence of Derf I, Derp I or Derp II was determined.

A microtiter plate on which 15E11 was immobilized as described in (2) of Example 1 was prepared. A solution which was prepared with PBS-Tween in the presence of Derf II in an amount of 0.3 µg/ml and Derf I, Derp I or Derp II in a concentration of 0–30 µg/ml was added to each well in an amount of 50 µl. Each well was incubated for two hours at room temperature and washed with PBS-Tween. 100 µl of a substrate solution was added to each well to color. The wells were reacted at room temperature for ten minutes 50 µl of 5N NaOH was added to each well to stop the reaction. The absorbance was determined at a wavelength of 405 nm with an autoreader. The results show that Derf II alone was apparently detected in spite of the presence of Derf I, Derp I and Derp II (referred to FIG. 4).

EXAMPLE 6

Relation of numbers of house dust mite bodies and absorbance by an immunoassay in which monoclonal antibodies, 15E11 and 13A4* were employed.

As described in (2) of Example 1, a microtiter plate to which 15E11 was immobilized was prepared. To extract mite allergen, each 500 µl of PBS-Tween containing 0 to 100 house dust mites (*D. farinae*) was stirred for ten seconds and allowed to stand ten minutes, and then centrifuged for two minutes at 1000 rpm. Each 50 µl of the supernatant was added to each well. Each well was incubated at room temperature for two hours and washed with PBS-Tween three times. 50 µl of a PBS-Tween solution prepared with 9 µg/ml of 13A4* was added to each well, respectively. Each well was incubated at room temperature for two hours and washed with PBS-Tween for three times. 100 µl of a substrate solution was added to each well. Each well was allowed to react at room temperature for ten minutes, and 50 µl of 5N NaOH was added to stop the reaction. The absorbance of each well was determined at 405 nm with an autoreader. The results are shown in FIG. 5. The absorbance determined was proportional to the numbers of the mite bodies. From the results, it was found that the numbers of mite bodies in sample can be estimated from the absorbance determined.

EXAMPLE 7

Derf II was purified from the freeze-dried mite bodies by affinity chromatography with gel in which the monoclonal antibody 13A4 which was obtained in (1) of Example 1 was employed as a ligand.

1.5 g of CNBr-Sepharose (manufactured by Pharmacia company) was swelled in 1mM HCl and thoroughly washed with a buffer of $0.1M$ NaHCO$_3$–$0.5M$ NaCl of PH 8.3 (abbreviated as a C buffer hereinafter). 5ml of a 13A4 (732 µg/ml) solution which was previously dialyzed against a C buffer and 20 ml of the C buffer were added to the gel and shaken at room temperature for two hours.

The reactant was centrifuged for 10 minutes at 2,500 rpm. Twenty five milliliters of a 0.2M glycine buffer, pH8.0 was added to the gel and the mixture was shaken at room temperature for two hours. The mixture was then centrifuged for 10 minutes at 2,500 rpm. The gel obtained was alternatingly washed with a C-buffer and a 0.1M acetic acid-0.5M NaCl buffer pH 4.0, two times, and then washed with PBS two times. The gel was charged into a plastic syringe to obtain a column. The column was alternatingly washed with a 0.2M glycine HCl buffer pH 2.3 (abbreviated as an elution buffer hereinafter) and a PBS-0.5M NaCl buffer (abbreviated as an washing buffer hereinafter), and then the column was equilibrated with a washing buffer. 0.05 g of freeze-dried mites bodies was dissolved in 500 μl of PBS, the solution was filtered with a 0.3 μ filter (MILLEX (trade mark); manufactured by Milipore Ltd.) and 500 μl of the filtrate was added to the column.

In a condition of a flow rate of 92 seconds/ml, the column was washed with a washing buffer, and Derf II was eluted with an elution buffer. The absorbance of each fraction was determined at a wave length of 280 nm. Each fraction was examined by SDS-PAGE, at the same time, the amount of Derf II in each fraction was determined by immunoassay with 15E11 and 13A4* of the monoclonal antibodies employed in Example 2. The results apparently show that only Derf II contained in the freeze-dried mites bodies was specifically absorbed to the gel. Accordingly, Derf II can be prepared by one step from the freeze-dried mites (referred to FIGS. 6 and 7).

EXAMPLE 8

The amount of Derf II in house dust was determined with a kit comprising monoclonal antibodies obtained in (1) of Example 1.

As an example, the kit was constituted as follows:

1 1) Primary antibody coating plate (abbreviated as a plate hereinafter),
2) Vessel for extracting antibodies (abbreviated as a vessel hereinafter),
3) Washing solution,
4) Enzyme-labeled secondary antibody solution,
5) Color producing substrate,
6) Substrate dissolving liquid,
7) Reaction stopping liquid, and
8) Standard Derf II.

House dust samples were obtained by absorbing house dust for three minutes or more at unspecified places with unspecified commercially available electric vacuum cleaners. The house dust obtained were divided into about 0.05 to 0.1 g to charge in vessels. The vessels were shaken and allowed to stand for ten minutes so as to obtain extracts 50 μl of the extract was added dropwise in each plate well. After incubating at room temperature for two hours, the plate was washed with a washing solution. 50 μl of a mixture containing 5 ml of the washing solution and one drop of an enzyme-labeled secondary antibody solution was added dropwise in each well of the plate and the wells were incubated at room temperature for two hours. After washing the plate with the washing solution, 100 μl of a solution containing one tablet of color producing substrate in 5 ml of a substrate dissolving liquid was added to each well. After ten minutes at room temperature, 50 μl of a reaction stopping liquid was added to the wells, and absorbance of each well was determined at a wave length of 405nm. In the same method, by using a solution in which standard Derf II was diluted with the washing solution, the calibration curve of Derf II was obtained.

Fifty percent ethanol was added to the house dust remaining in the vessel to wash and recover the house dust. The house dust solution was filtered through stainless meshes (355 μ). Methylene blue was added to the filtrate to obtain a concentration of a 1% methylene blue solution. The solution was filtered through 80 μm filters (manufactured by Fuji Photo Film Company, microfilters) to recover the mites under a stereoscopic microscope of 20 magnifications. The mite preparate was obtained by a chloral hydrate method and the identified mites in the house dust were counted.

The amount of Derf II and numbers of the mites in the house dust were interrelated.

We claim:

1. An anti Derf II monoclonal antibody selectively binding to Derf II alone and not binding to Derp I, Derp II and Derf I, wherein said monolonal antibody is produced by hybridoma cell line 15E11 (FERM BP-3249) or 13A4 (FERM BP-3251).

2. An immunoassay for selectively detecting Derf II but not detecting Derp I, Derf I and Derp II, comprising contacting a monoclonal antibody in accordance with claim 1, with a sample suspected of containing Derf II and determining the presence of a reaction between said monoclonal antibody with any Derf II in the sample.

3. A kit for selectively detecting Derf II and not detecting Derp I, Derf I and Derp II, by the immunoassay, comprising a monoclonal antibody in accordance with claim 1, a solid phase carrier for said monoclonal antibody, a blocking agent, a labeled anti-(mouse Ig) antibody, a color producing substrate, a washing solution and standard Derf II.

4. A hybridoma cell line which produces an anti Derf II monoclonal antibody selectively binding to Derf II along and not binding to Derp I, Derp II and Derf I, wherein the hybridoma cell line is 15E11 (FERM BP-3249) or 13A4 (FERM BP-3251).

* * * * *